(12) United States Patent
Hendrixson

(10) Patent No.: US 7,204,703 B1
(45) Date of Patent: Apr. 17, 2007

(54) EPICARDIAL PACER EXTENSION CABLE SYSTEM

(75) Inventor: Paul Hendrixson, Cumming, GA (US)

(73) Assignee: Remington Medical, Inc., Alpharetta, GA (US)

( * ) Notice: Subject to any disclaimer, the term of this patent is extended or adjusted under 35 U.S.C. 154(b) by 0 days.

(21) Appl. No.: 11/445,019

(22) Filed: Jun. 1, 2006

Related U.S. Application Data

(62) Division of application No. 11/063,935, filed on Feb. 23, 2005, now Pat. No. 7,059,878.

(60) Provisional application No. 60/579,332, filed on Jun. 14, 2004.

(51) Int. Cl.
H01R 29/00 (2006.01)

(52) U.S. Cl. ............ 439/171; 439/909; 439/263

(58) Field of Classification Search ........ 439/171, 439/909, 263, 173, 174, 259; 607/37, 116, 607/119, 122

See application file for complete search history.

(56) References Cited

U.S. PATENT DOCUMENTS

| 1,530,011 | A |   | 3/1925  | Pacet |
| 1,536,688 | A | * | 5/1925  | Osborn ............ 439/263 |
| 2,496,173 | A |   | 1/1950  | Peebles |
| 3,891,289 | A | * | 6/1975  | Hanke ............ 439/106 |
| 4,466,690 | A |   | 8/1984  | Osypka |
| 4,627,681 | A | * | 12/1986 | Hong ............ 439/370 |
| 4,764,132 | A |   | 8/1988  | Stutz, Jr. |
| 4,951,687 | A |   | 8/1990  | Ufford et al. |
| 5,086,773 | A |   | 2/1992  | Ware |
| 5,106,317 | A |   | 4/1992  | Taylor |
| 5,257,622 | A |   | 11/1993 | Hooper et al. |
| 5,286,213 | A | * | 2/1994  | Altergott et al. ............ 439/139 |
| 5,904,587 | A |   | 5/1999  | Osypka et al. |
| 6,162,101 | A |   | 12/2000 | Fischer et al. |
| 6,167,314 | A |   | 12/2000 | Fischer, Sr. et al. |
| 6,183,305 | B1 |  | 2/2001  | Doan et al. |
| 6,729,895 | B1 | * | 5/2004 | Bryan ............ 439/263 |
| 6,847,845 | B2 |  | 1/2005  | Belden |
| 6,871,101 | B2 |  | 3/2005  | Zhang et al. |
| 6,878,013 | B1 |  | 4/2005  | Behan |
| 6,910,906 | B2 |  | 6/2005  | Schorn |
| 6,984,145 | B1 |  | 1/2006  | Lim |
| 2004/0082866 | A1 | | 4/2004 | Mott et al. |

* cited by examiner

Primary Examiner—Gary F. Paumen
(74) Attorney, Agent, or Firm—Womble, Carlyle, Sandridge & Rice, PLLC

(57) ABSTRACT

The invention provides an extension cable system for connecting electrodes to a medical device such as an External Pacing Generator. The system further provides a connector separator for maintaining electrode receiving connectors in a fixed relationship relative to each other to avoid contact between electrically exposed regions of the electrodes. The extension cable system comprises electrically conductive leads electrically connected to a plug adapted to an electrical socket of a medical device, dielectrically shrouded electrode receiving connector(s) that form an electrical connection with a filamentous electrode or electrically conductive wire, and a connector separator for gripping and maintaining the electrode receiving connectors in a predetermined and rigid relationship relative to each other. The electrode receiving connectors comprise outer shrouds that can be threadably rotated to operate wire receiving chucks to receive electrode wires. The connector separator comprises a bridge having opposing ends adapted as bifurcated grips for gripping an electrode receiving connector.

2 Claims, 4 Drawing Sheets

EPICARDIAL PACER EXTENSION CABLE SYSTEM

CROSS REFERENCE TO RELATED APPLICATIONS

This application is a divisional of and claims the benefit of U.S. patent application Ser. No. 11/063,935, filed Feb. 23, 2005 now U.S. Pat. No. 7,059,878, and U.S. Provisional Application No. 60/579,332, filed Jun. 14, 2004 (Hendrixson, Disposable Pacemaker Lead System and Kit), which are hereby incorporated herein by reference in their entirety.

FIELD OF THE INVENTION

The present invention relates to an extension cable system for connecting electrodes to a medical device. The invention further relates to a separator for maintaining electrode receiving connectors in a fixed relationship.

BACKGROUND

A number of medical devices, cardiac pacemakers for example, are intended to deliver or receive an electric current to a patient. However, inadvertent current discharge to a patient or to attending medical personnel is sometimes possible because of exposed or uninsulated electrical connectors or plugs that electrically link the power source to the electrodes contacting the patient. The electrodes themselves may also have uninsulated regions that can touch one another while being implanted into the patient, or due to bad positioning or being moved leading to short circuits, equipment damage and possible patient injury.

Regulatory mandates require that connections, connectors or connector pins on electrical leads that are to be connected to a medical device such as an External Pacer Generator ("EPG"), be shrouded with dielectric material. However, the insulating shrouds placed around connector pins can be incompatible with the corresponding receiving connectors that are installed in adapters located at the ends of the extension cables that connect to the current generator.

Some manufactures provide supplementary extension pins that reach beyond the insulating protective shrouds to insert into an extension cable adapter. However, although the connectors themselves still remain shrouded, the pin extensions are now exposed, and reintroduce the possibility of unintended electrical contact between the pins causing a short circuit or with the patient. The extension pins also can be readily disengaged from the medical device extension cable adapter even during patient treatment and with a pulling force less than the minimum mandated by federal regulations.

To meet the regulatory requirements, medical device extension cable adapters have been modified to receive shrouded connectors without the need for additional extension pins. A locking attachment such as that used in the ADAP-2000/PACE-LOC™ system (Remington Medical, inc, Alpharetta, Ga.) ensures that the shrouded connectors cannot disengage the adapter without removing the lock and applying significant force. These connection locking systems, however, are expensive and complex to manufacture.

There is still a need, therefore, for a means of electrically connecting wire electrodes to a medical device that does not require an intervening cable adapter. There is also a need to prevent uninsulated and conductive regions of the wire electrodes that enter the patient from self-contacting and short circuiting or injuring the patient by directly contacting the skin rather than delivering the current to the intended target organ.

SUMMARY OF THE INVENTION

The present invention provides an extension cable system for connecting electrodes to any medical device such as, but not limited to, electrocardiographs, arrhythmia detectors, cardiac monitors. The extension cables of the invention, however, are especially useful for electrically connecting epicardial wire electrodes to an External Pacing Generator (EPG) to electrode wires. The system further provides a connector separator for maintaining electrode receiving connectors and wire electrodes in a fixed relationship relative to each other to avoid contact between electrically exposed regions of the electrodes, thereby reducing the risks of short circuits and harm to the patient, the medical device, or both.

The invention provides an extension cable system comprising a pair of leads connected to a plug adapted to connect to the input socket of a medical device, dielectrically shrouded electrode receiving connector(s) connected to the leads and designed to make an electrical connection with a filamentous electrode or electrically conductive wire, and a connector separator for gripping and maintaining the electrode receiving connectors in a predetermined and rigid relationship relative to each other, thereby reducing the possibility of inadvertent contact and short circuit between non-electrically insulated regions of the inserted electrode wires. The electrode receiving connectors comprise outer shrouds that can be threadably rotated to open wire receiving chucks to receive electrode wires. The shrouds are then counter-turned to tighten the chucks against the wires.

Another aspect of the invention provides a connector separator comprising a bridge having opposing ends adapted as bifurcated grips, each grip defining a connector receiving channel for gripping an electrode receiving connector.

The extension cable system of the invention can also be provided as a kit in an enclosed envelope that maintains sterility of the internal contents prior to using the system with a patient. The system components can be separate or partially or totally assembled before sealing in the envelop and/or sterilizing.

FIGURES

FIG. 1. illustrates an extension cable system according to the present invention for connecting a medical device to electrode wires.

FIG. 2 illustrates a vertical section through an embodiment of the electrode receiving connector.

FIG. 3. illustrates a connector separator with hexagonal channels of the bifurcated grips.

DESCRIPTION OF THE INVENTION

Figure 1:
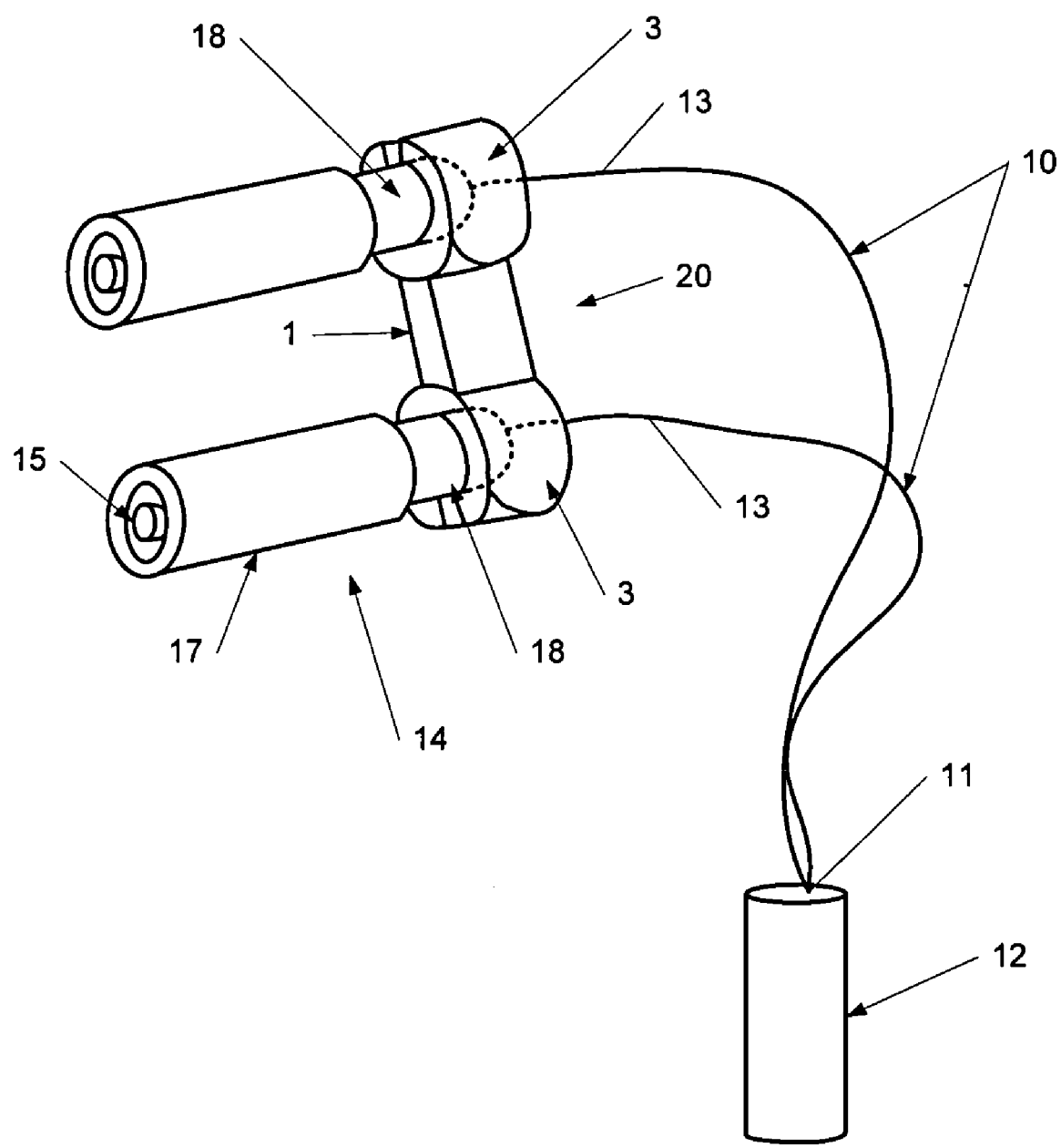

A full and enabling disclosure of the present invention, including the best mode known to the inventor of carrying out the invention, is set forth more particularly in the remainder of the specification, including reference to the accompanying drawings, wherein like reference numerals designate corresponding parts throughout several figures.

This description is made for the purpose of illustrating the general principles of the invention and should not be taken in the limiting sense.

The present invention provides an extension cable system suitable for electrically connecting epicardial wire electrodes to an EPG. It is contemplated, however, that the extension cable system of the present invention is also useful for connecting other external medical devices such as, but not limited to, electrocardiographs, arrhythmia detectors, cardiac monitors, and the like, to electrode wires. The system further provides a connector separator for maintaining the electrode receiving connectors and their attached wire electrodes in a fixed configuration relative to each other to prevent contact between any electrically exposed regions of the electrodes, thereby reducing the risks of short circuits and harm to the patient, the medical device, or both.

One aspect of the invention, as illustrated in FIG. 1, is an extension cable system comprising a pair of electrically conductive leads 10, of which the distal ends 11 relative to the patient are electrically connected to a plug 12 adapted to an electrical socket, such as an output socket, of a medical device. In one embodiment of the invention, the plug 12 is adapted to fit the output socket of an EPG. In another embodiment, each lead 10 has a plug 12 for electrically connecting the leads 10 to individual output positive and negative terminals of a device. The proximal end 13 of each lead 10 relative to the patient is electrically connected to an electrode receiving connector 14. The electrode receiving connector 14 according to the present invention is adapted for receiving and forming a secure electrical connection with a filamentous electrode or electrically conductive wire that is connected to a patient.

Figure 2:
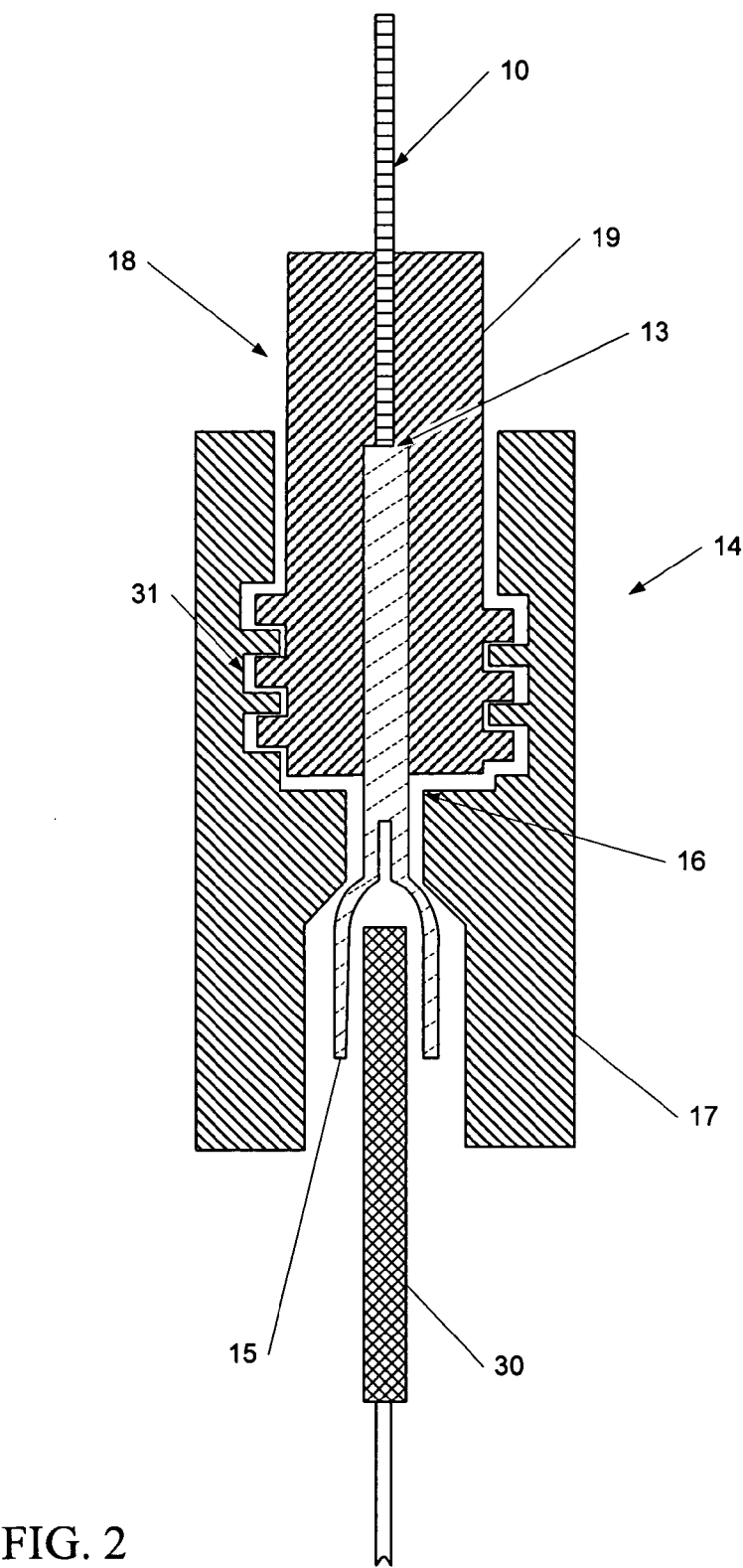

In one embodiment of the invention, the electrode receiving connector 14 is adapted to receive and grip an epicardial wire. In this embodiment, as illustrated in FIG. 2, the electrode receiving connector 14 comprises a dielectric non-conductive body 19 having at the proximal end 16 a wire receiving chuck 15 surrounded by a dielectric outer shroud 17. The outer shroud 17 is threadably engaged with the body 19 by a screw thread 31 such that when rotationally adjusted, the outer shroud 17 will tighten or loosen the chuck 15 against an electrode wire 30 inserted therein. The distal region 18 of body 19 of the electrode receiving connector 14 extends beyond the outer shroud 17, and receives the proximal end 13 of a lead 10 which is electrically connected to the chuck 15. Distal region 18 may be of any cross-sectional geometry including, but not limited to, a square, a rectangle, a hexagon and an octagon.

Figure 3:
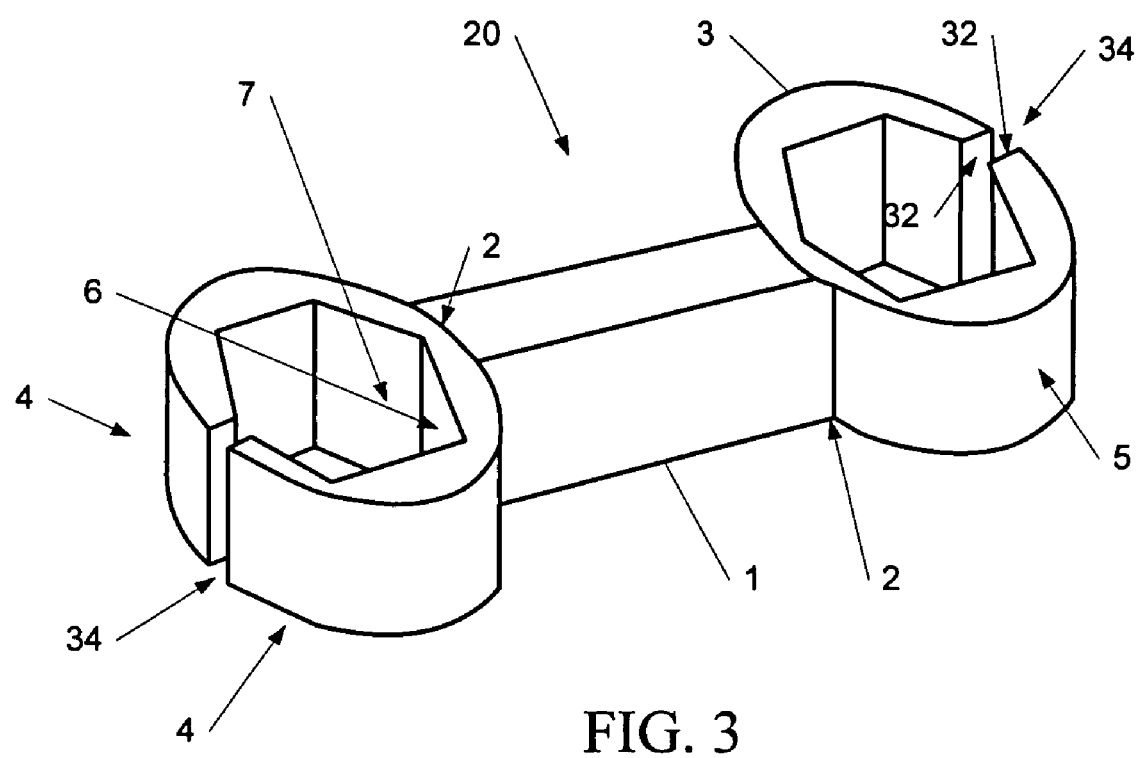

The extension cable system of the invention also comprises a connector separator 20 for gripping and maintaining the electrode receiving connectors 14 in a predetermined and rigid relationship relative to each other. As illustrated in FIG. 3, for example, the connector separator 20 comprises a bridge 1 having opposing ends 2, each end 2 having a bifurcated grip 3. The separator 20 can be manufactured from any material that can be sterilized, including by chemical or radiation methods. The separator 20 can be molded as a single unit, as illustrated in FIG. 3, or as a multi-component adjustable unit as illustrated, for example, in FIGS. 4A and 4B.

Each bifurcated grip 3 of the separator 20 comprises at least two extended opposing arms 4, each arm having an outer surface 5 and an inner surface 6, said inner opposing surfaces 6 defining a connector receiving channel 7. The extended arms 4 of each grip 3 have resilience to provide a gripping force directed against the distal region 18 of an electrode receiving connector 14 inserted into the connector receiving channel 7 of the grip 3. Preferably the connector receiving channel 7 is compatible with the cross-section of the distal end 18 of the electrode receiving connector 14. In one embodiment of the system of the invention, the grip(s) 3 are not resilient and the distal region 18 of the body 19 is resilient so as to exert a force against a grip 3 when inserted in connector receiving channel 7.

Figure 4A:
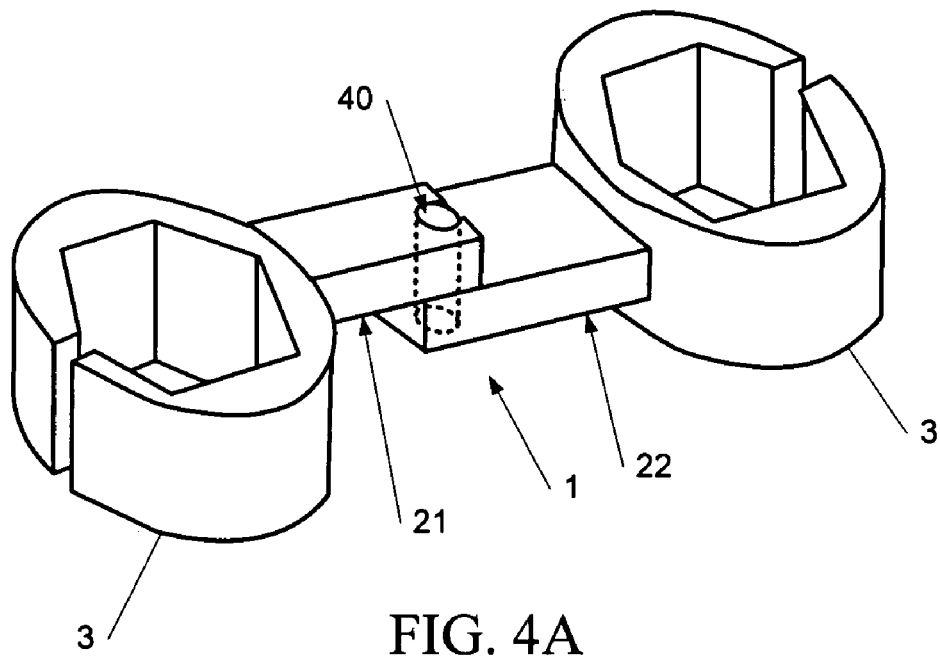
FIG. 4A illustrates an adjustable separator according to the present invention.
Figure 4B:
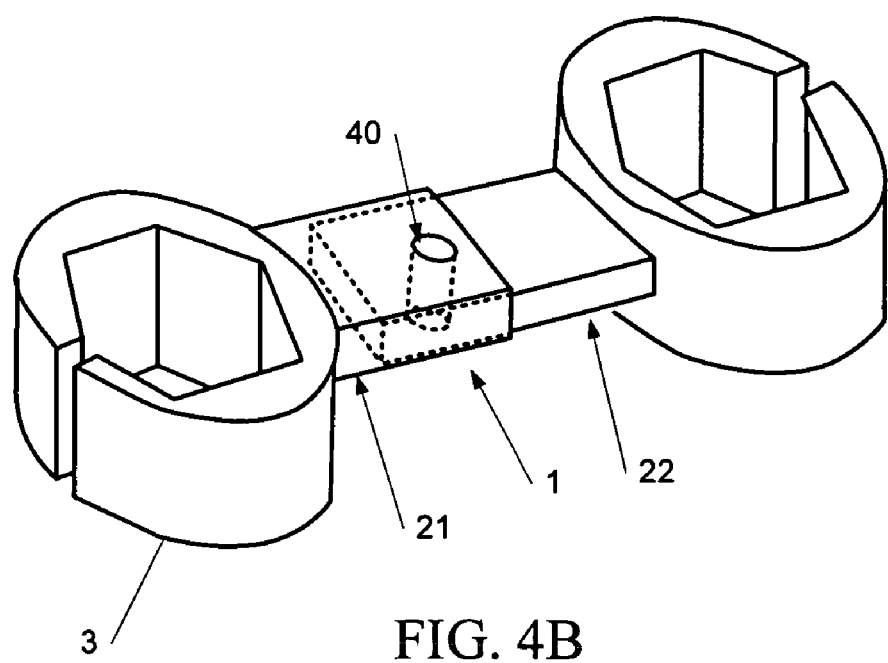
FIG. 4B illustrates another embodiment of the adjustable separator according to the present invention.

The bridge 1 of the separator 20 can have any cross-sectional geometry including, but not limited to, square, rectangular, or circular. The bridge 1 can be adjustable to vary the distance separating the electrode receiving connectors 14. In one embodiment of the separator 20 of the invention, the bridge 1 comprises a first extension 21 extending from a first grip 3 and a second extension 22 extending from a second grip 3, as illustrated in FIG. 4A. The overlapping extensions 21, 22 can be slideably engaged to adjust the separation distance between the grips 3. A means 40 of locking the overlapping extensions together to secure the two extensions 21 and 22 of the separator 20, such as a tightening screw can be provided. In one embodiment of the separator 20 of the invention as illustrated in FIG. 4A, the extensions 21, 22 are layered. In another embodiment, as illustrated in FIG. 4B, extension 21 is a tube that can slideably receive the extension 22.

The extension cable system of the invention can be provided as a kit in an enclosed container, such as an envelope, that will maintain sterility of the internal contents prior to using the system with a patient. The system components can be disassembled or partially or totally assembled before they are sealed in the container and optionally sterilized. The plug(s) 13 and electrode receiving connector(s) 14 typically will be electrically connected to the distal 11 and proximal 12 ends of the leads 10 respectively, before placing in the envelope.

To assemble the extension cable system according to the invention, individual leads 10 can be passed through gaps 34 between distal ends 32 of the arms of bifurcated grips 3 and into the connector receiving channel channels 7 as illustrated in FIG. 1. The distal ends 18 of the electrode receiving connectors 14 attached to the leads 10 can then be pushed into the receiving channel channels 7. The width of the connector receiving channels 7 in at least one direction should exceed the diameter of the distal end 18 to allow the resilient grip 3 to apply a gripping force to the connector 14. The outer shrouds 17 of the connectors 14 can be threadably rotated around screw 31 to open the wire receiving chucks 15 to receive the distal ends of electrode wires 30. The shrouds 17 are then counter-turned to tighten the chucks 15 against the electrode wires 30 thereby forming an electrical connection between the inserted wires 30 and the leads 10. The plug(s) 12 at the distal ends of the leads 10 can then be inserted into a suitable electrical socket(s) of the medical device to establish electrical connections between the medical device and the electrode wires 30. Typically, if the electrode wires 30 are epicardial wires, they are implanted into the thoracic cavity of a patient to contact cardiac tissue before inserting the distal ends thereof into the electrode receiving connectors 14.

With respect to the above description, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawing and described in the specification are intended to be encompassed by the present invention. Further, the various components of the embodiments of the invention may be interchanged to produce further embodiments and these further embodiments are intended to be encompassed by the present invention.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for electrically insolating medical electrodes comprising:

connecting one end of a pair of leads to a plug for a medical device;

connecting the opposite ends of said leads to electrodes receiving connectors;

inserting and locking said medical electrodes in said connectors; and electrically and physically isolating said connectors from one another, comprising:

inserting said connectors into bifurcated grips made of a dielectric material;

connecting said bifurcated grips with a bridge made of a dielectric material;

locking said connectors in place in said bifurcated grips.

2. The method of claim 1 and further comprising, passing said leads through gaps formed in said bifurcated grips.

* * * * *